United States Patent
Pristinski

(10) Patent No.: US 9,846,111 B2
(45) Date of Patent: Dec. 19, 2017

(54) OPTICAL DETECTION SYSTEM FOR PARTICLES

(71) Applicant: Bio-Rad Laboratories, Inc., Hercules, CA (US)

(72) Inventor: Denis Pristinski, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/394,605

(22) Filed: Dec. 29, 2016

(65) Prior Publication Data

US 2017/0191924 A1    Jul. 6, 2017

Related U.S. Application Data

(60) Provisional application No. 62/273,362, filed on Dec. 30, 2015.

(51) Int. Cl.
*G01N 21/64* (2006.01)
*G01N 15/14* (2006.01)

(52) U.S. Cl.
CPC ..... *G01N 15/1434* (2013.01); *G01N 15/1404* (2013.01); *G01N 15/1459* (2013.01); *G01N 21/6428* (2013.01); *G01N 2015/1409* (2013.01)

(58) Field of Classification Search
CPC ............... G01N 15/02; G01N 15/0211; G01N 15/0205; G01N 15/1459; G01N 15/1404; G01N 15/1436; G01N 2015/1493; G01N 2015/1497; G01N 21/05
USPC .......................................... 356/335–343, 73
See application file for complete search history.

(56) References Cited

U.S. PATENT DOCUMENTS

| | | | | |
|---|---|---|---|---|
| 4,715,708 A | * | 12/1987 | Ito | G01N 15/1434 250/201.4 |
| 5,684,584 A | * | 11/1997 | Nakamoto | G01N 15/14 356/336 |
| 5,872,627 A | * | 2/1999 | Miers | G01N 15/1431 356/338 |

(Continued)

FOREIGN PATENT DOCUMENTS

| | | |
|---|---|---|
| WO | 2013189921 A1 | 12/2013 |
| WO | 2014186228 A1 | 11/2014 |

OTHER PUBLICATIONS

Young, Lee W., Authorized Officer, ISA/US Commissioner for Patents, "International Search Report" in connection with related International Application No. PCT/US2016/069332, dated Apr. 21, 2017, 2 pages.

(Continued)

*Primary Examiner* — Hoa Pham
(74) *Attorney, Agent, or Firm* — Kolisch Hartwell, P.C.

(57) ABSTRACT

Optical detection system and method for particles. In exemplary embodiments, the system may comprise a channel, a light source configured to generate light, and one or more optical elements configured to focus a beam of the light on an irradiation zone within the channel. The system also may comprise a mask operatively disposed in an optical path between the light source and the channel. The mask may be configured to block a portion of the beam, thereby producing a shadow region. The system further may comprise a detector configured to detect light deflected from the beam into the shadow region by interaction with a particle passing through the irradiation zone.

17 Claims, 9 Drawing Sheets

(56) References Cited

U.S. PATENT DOCUMENTS

| | | | |
|---|---|---|---|
| 6,023,324 | A | 2/2000 | Myers |
| 6,180,415 | B1 * | 1/2001 | Schultz ................. B82Y 30/00 356/301 |
| 2008/0138848 | A1 | 6/2008 | Li et al. |
| 2008/0246946 | A1 * | 10/2008 | Hansen .............. G01N 15/1459 356/36 |
| 2010/0173394 | A1 | 7/2010 | Colston, Jr. et al. |
| 2012/0194805 | A1 | 8/2012 | Ness et al. |
| 2012/0252015 | A1 | 10/2012 | Hindson et al. |
| 2014/0221239 | A1 | 8/2014 | Carman et al. |
| 2014/0370586 | A1 | 12/2014 | Seo et al. |

OTHER PUBLICATIONS

Young, Lee W., Authorized Officer, ISA/US Commissioner for Patents, "Written Opinion of the International Searching Authority" in connection with related International Application No. PCT/US2016/069332, dated Apr. 21, 2017, 7 pages.

* cited by examiner

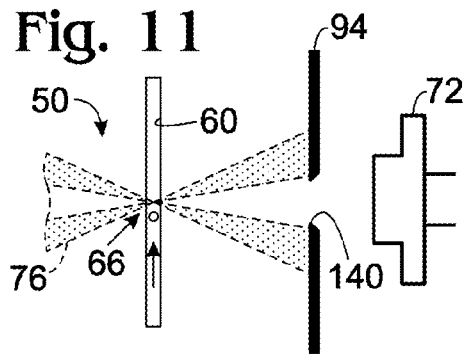
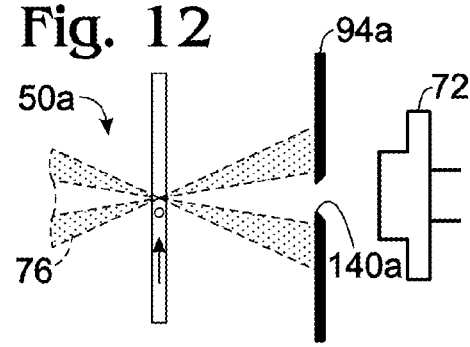
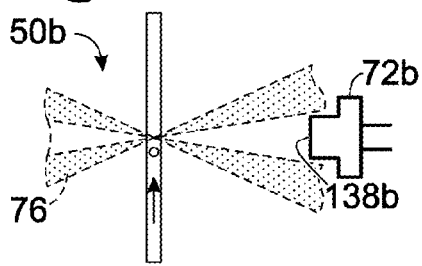
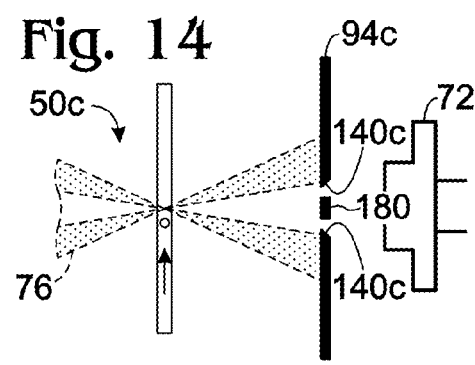
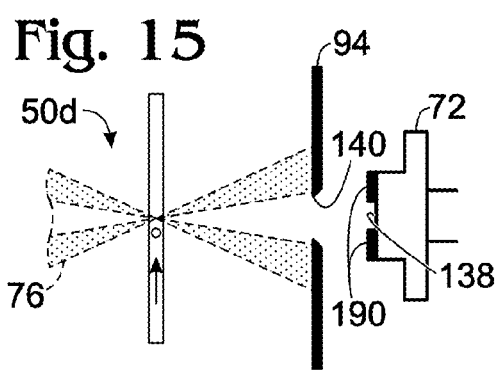

OPTICAL DETECTION SYSTEM FOR PARTICLES

CROSS-REFERENCE TO PRIORITY APPLICATION

This application is based upon and claims the benefit under 35 U.S.C. §119(e) of U.S. Provisional Patent Application Ser. No. 62/273,362, filed Dec. 30, 2015, which is incorporated herein by reference in its entirety for all purposes.

CROSS-REFERENCES TO OTHER MATERIALS

This application incorporates by reference in their entirety for all purposes the following: U.S. Patent Application Publication No. 2010/0173394 A1, published Jul. 8, 2010; and Joseph R. Lakowicz, PRINCIPLES OF FLUORESCENCE SPECTROSCOPY ($2^{nd}$ Ed. 1999).

INTRODUCTION

A signal is detected from particles in various types of assays. The particles may be solid-phase particles (e.g., beads), liquid-phase particles (droplets), or biological cells, among others. In a typical assay, the particles are labeled with a fluorescent dye. Fluorescence then is detected from individual particles as the particles are passed serially through a detection volume where the fluorescent dye is excited to cause light emission.

Fluorescence alone may be inadequate to accurately detect the presence of each particle and characterize the particle's size/shape. This problem can be significant in a mixed population of particles each having high or low fluorescence, as in many digital assays, and/or when some of the particles should be ignored for being too large or small or for having an aberrant shape. Accordingly, the result of a particle-based assay may be skewed by overestimating or underestimating the number of particles detected, failing to exclude fluorescence data for particles that do not meet size/shape criteria, and the like.

Cell sorting instruments have been developed that detect light scattering by, and fluorescence from, biological cells traveling through a flow cell. The ability of each cell to scatter light allows the presence of the cell to be detected, while a fluorescence signal detected from the cell provides further characterization. The instrument utilizes a laser beam to irradiate a region of the flow cell, and positions an opaque optical stop behind the flow cell. The stop blocks undeflected light of the beam, while scattered light bypasses the optical stop and is detected by a scattering detector located beyond the optical stop. A condenser with a long focal length focuses the laser beam onto the flow cell, which makes epi-fluorescence detection impractical. Instead, light emitted by fluorescence is collected and detected in an optical path extending from the flow cell in a direction orthogonal to the excitation path followed by the laser beam to the flow cell.

The design of these cell sorting instruments has various disadvantages. For example, the laser is expensive and can make the instrument unaffordable for a typical laboratory. Also, the flow cell must be optically accessible on three sides, which severely limits the options for replacing the flow cell with a different fluidic member.

SUMMARY

The present disclosure provides an optical detection system and method for particles. In exemplary embodiments, the system may comprise a channel, a light source configured to generate light, and one or more optical elements configured to focus a beam of the light on an irradiation zone within the channel. The system also may comprise a mask operatively disposed in an optical path between the light source and the channel. The mask may be configured to block a portion of the beam, thereby producing a shadow region. The system further may comprise a detector configured to detect light deflected from the beam into the shadow region by interaction with a particle passing through the irradiation zone.

BRIEF DESCRIPTION OF THE DRAWINGS

FIG. 11 is a fragmentary view of the detection system of FIG. 1 taken around a flow channel and a deflection detector of the system.

FIG. 12 is a fragmentary view of a modified version of the detection system of FIG. 1, taken as in FIG. 11 and having a narrower optical slit between the flow channel and the deflection detector, to reduce detection of small angle deflection.

FIG. 13 is a fragmentary view of another modified version of the detection system of FIG. 1, taken as in FIG. 11 and having a deflection detector with a smaller photosensitive area located in the image plane of the mask and replacing the optical slit of FIG. 11.

FIG. 14 is a fragmentary view of still another modified version of the detection system of FIG. 1, taken as in FIG. 11 and having a pair of optical slits located in the image plane of the mask to reduce detection of large angle deflection.

FIG. 15 is a fragmentary view of yet another modified version of the detection system of FIG. 1, taken as in FIG. 11 and having a portion of the deflection detector masked to reduce detection of undesired light.

DETAILED DESCRIPTION

Figure 1:
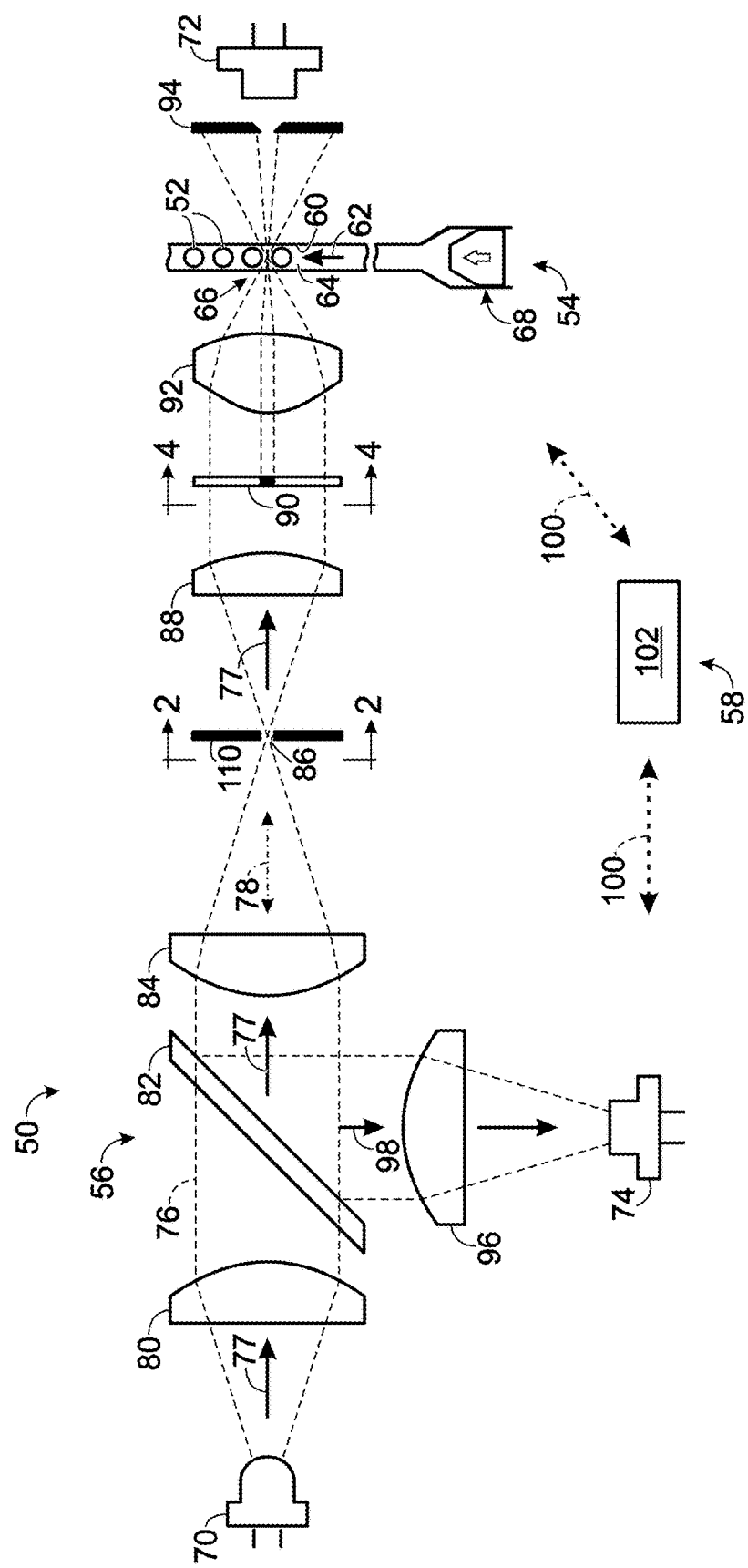
FIG. 1 is a schematic view of an exemplary optical detection system for detecting and characterizing particles, such as droplets, in accordance with aspects of the present disclosure.

The present disclosure provides an optical detection system and method for particles. In exemplary embodiments, the system may comprise a channel, a light source configured to generate light, and one or more optical elements configured to focus a beam of the light on an irradiation zone within the channel. The system also may comprise a mask operatively disposed in an optical path between the light source and the channel. The mask may be configured to block a portion of the beam, thereby producing a shadow region. The system further may comprise a detector configured to detect light deflected from the beam into the shadow region by interaction with a particle passing through the irradiation zone.

In some embodiments, the system may comprise an optical slit operatively disposed in an optical path between the light source and the channel. At least one collimating element may be operatively disposed in the optical path upstream of the mask, such that the mask intersects a collimated region of the beam. The mask may be a line mask having an elongated masking region oriented parallel to the optical slit and configured to block a portion of the collimated region of the beam. One or more focusing elements may be operatively disposed in an optical path between the mask and the channel and configured to focus the beam on the irradiation zone. Furthermore, the particle may be a droplet, a solid-phase particle, or a biological cell. In some embodiments, the particle may be a droplet suspended in an immiscible carrier liquid.

An exemplary method of detecting a particle is provided. In the method, a beam of light may be generated. A transverse (cross-sectional) portion of the beam may be blocked optically upstream of a channel to produce a shadow region. The beam may be focused on an irradiation zone within the channel. A particle may be passed through the irradiation zone. The step of passing may deflect light into the shadow region by interaction with the particle. Deflected light may be detected in the shadow region. The step of passing may cause more light to be detected temporarily, optionally as a pulse of increased light intensity.

The method may be defined further. The step of focusing may be performed on a partially blocked region of the beam that results from the step of blocking. The step of blocking may be performed on a collimated region of the beam. The method further may comprise a step of passing light of the beam through an optical slit operatively disposed such that the step of passing light is performed optically upstream of the step of blocking a portion of the beam. The beam may include optical radiation emitted by a light-emitting diode. The step of blocking may be performed with a line mask. The line mask may have a masking region elongated orthogonal to the channel. The masking region may be elongated parallel to an optical slit operatively disposed upstream of the line mask. The step of detecting may be performed with a detector, and the method further may comprise a step of spatially filtering light of the beam with an optical slit disposed in an optical path between the channel and the detector. The method further may comprise a step of detecting photoluminescence induced by the beam at the irradiation zone. The step of passing a particle may include a step of passing a droplet through the irradiation zone. The step of blocking may be performed with a mask, and the step of detecting may detect light received from an optical slit located in an image plane of the mask. The step of detecting may be performed with a detector, and the light detected in the shadow region may not be focused between the channel and the detector.

Further aspects of the present disclosure are described in the following sections: (I) detection system overview, (II) fluidics subsystem, (III) optical subsystem, (IV) methods of particle detection, and (V) examples.

I. DETECTION SYSTEM OVERVIEW

This section provides an overview of an exemplary detection system 50 for optically detecting and/or characterizing particles 52, such as droplets; see FIGS. 1-8. Detection system 50 may include a fluidics subsystem 54, an optical subsystem 56, and a processing/control subsystem 58.

Fluidics subsystem 54 may incorporate a channel 60 at which the fluidics subsystem intersects the optical subsystem. The channel defines a flow path for travel, indicated by a motion arrow at 62, of particles 52 and a surrounding carrier fluid 64. The flow path extends through an irradiation zone 66 within the channel. (The irradiation zone 66 interchangeably may be called a detection volume, as explained below.) The fluidics subsystem also includes a drive mechanism operatively connected to the channel and including one or more sources of positive/negative pressure. Each source of positive/negative pressure may, for example, include at least one pump 68 that is operatively connected to the channel, to create a pressure differential that drives flow of the carrier fluid along channel 60 and through irradiation zone 66. The pump may be a positive pressure pump or a negative pressure pump (i.e., a vacuum pump). Fluid communication between the pump and the channel may be controlled by one or more valves located in a fluid path between the pump and the channel.

Particles 52 are transported by the carrier fluid through the irradiation zone. The carrier fluid may be supplied by a source of carrier fluid that is in fluid communication with the channel. In some embodiments, the particles may be droplets, such as aqueous droplets, and the carrier fluid may be a continuous phase, such as oil, composed of liquid that is immiscible with the droplets.

Optical subsystem 56 includes at least one light source 70, at least one light detector (e.g., a deflection detector 72 and a photoluminescence detector 74), and various optical elements to direct and/or restrict travel of optical radiation from the light source(s) to irradiation zone 66, and from the irradiation zone to the detector(s). Light source 70 generates a beam 76 of optical radiation, which may, for example, be diverging, collimated, or converging in regions along the beam, according to the optical elements disposed in the path of the beam. The optical subsystem may incorporate any suitable optical elements, such as lenses, masks, spatial/ spectral filters, mirrors, aperture-defining elements, beam splitters, light guides, and the like. For example, one or more spectral filters may be disposed in an optical path between the irradiation zone and the photoluminescence detector to selectively prevent excitation light (relative to light emitted by photoluminescence) from reaching the detector.

The terms "light" and "optical radiation" are used interchangeably in the present disclosure. Either term denotes ultraviolet radiation, visible light, or infrared radiation, or any combination thereof.

Beam 76 follows on an optical path 77 extending downstream from light source 70, across channel 60, and toward deflection detector 72. The optical path defines an optical axis 78 that may be linear, as shown here, or may be bent (e.g., via a light guide and/or a mirror) (see Example 3). In the depicted embodiment, following the beam from light source 70 along optical path 77, beam 76 diverges, is collimated by a collimating lens 80, extends through a beam splitter 82 (here, a short-pass mirror), and is focused by a focusing lens 84. The focused beam extends through an optical slit 86, is collimated by another collimating lens 88, and partially blocked by mask 90. The beam is focused by at least one focusing element on irradiation zone 66 of channel 60. The focusing element(s) may be described as a condenser and as an objective. The focusing element(s) functions as a condenser for optical radiation of beam 76 traveling from left to right in FIG. 1 along optical path 77, and as an objective for emitted light traveling in reverse, from right to left in FIG. 1, along only a portion of the optical path. The focusing element(s) is called objective 92.

At any given time, optical radiation incident on irradiation zone 66 may follow different trajectories. Most of the optical radiation of the beam may pass through irradiation zone 66 substantially undeflected. This undeflected optical radiation is not incident on the photosensitive region of deflection detector 72. For example, this undeflected optical radiation may be prevented from reaching detector 72 by a spatial filter, namely, an aperture-defining element (e.g., a slit-forming element 94), or may be too divergent from the optical path to detector 72. A fraction of the optical radiation may be deflected sufficiently toward the deflection detector by the current contents of the irradiation zone, such that the deflected radiation is incident on a photosensitive area of the detector and thus is detected. Another fraction of the optical radiation may excite a photoluminophore(s) within the irradiation zone, causing emission of photons (i.e., photoluminescence).

A portion of this emitted light may be detected by photoluminescence detector 74, after travel in reverse along a portion of optical path 77. In particular, the emitted light passes through objective 92, collimating (now focusing) lens 88, optical slit 86, and focusing (now collimating) lens 84. When the emitted light (of longer wavelength than the excitation light of beam 76) reaches beam splitter 82, the light is reflected to a focusing lens 96, indicated by an arrow at 98, which focuses the emitted light on photoluminescence detector 74. Accordingly, optical radiation from the same light source 70 may be deflected toward deflection detector 72 and may cause photoluminescence.

The term "deflect," as used herein, means cause to change course or follow a new trajectory. More specifically, optical radiation deflected by interaction with matter (e.g., a particle and/or carrier fluid) in an irradiation zone deviates from a current trajectory as a consequence of the interaction. Deflection may occur by any suitable mechanism or combination of mechanisms. Exemplary deflection mechanisms pertinent to the detection system disclosed herein may include refraction, reflection, Mie scattering, and the like. In some embodiments, such as with transparent particles, a difference in refractive index between the particles and the carrier fluid may be responsible for a majority of the detected deflection.

To facilitate description, light can be considered to travel in the beam along an optical path from positions optically "upstream" to positions optically "downstream." Accordingly, the relative position of optical elements in the optical path also can be described with these two terms. For example, in FIG. 1, light source 70 is upstream of optical slit 86, which, in turn, is upstream of mask 90. The mask is upstream of objective 92 and irradiation zone 66. Deflection detector 72 and slit-forming element 94 are downstream of irradiation zone 66, and slit-forming element 94 is upstream of detector 72.

Processing/control subsystem 58 may be in communication with and/or operatively connected to any suitable components of the fluidics subsystem and/or the optical subsystem, as indicated by arrows 100. For example, subsystem 58 may receive a deflection signal detected by deflection detector 72 and/or a photoluminescence signal detected by photoluminescence detector 74. Subsystem 58 may include a processor 102 (e.g., an electronic/digital processor) configured to process the deflection signal and/or the photoluminescence signal to determine one or more characteristics of particles 52. The characteristics may include a size, velocity, shape, transit time through the irradiation zone, presence or absence of an analyte in or on individual particles, or the like. Processor 102 also or alternatively may control operation of pump 68, light source 70, or one or both detectors 72 and 74, or any combination thereof.

Processor 102 may include a memory and a data manipulation program stored in the memory. The data manipulation program may include instructions stored in memory and executable by the processor to control and/or perform any of the steps of the present disclosure.

Figure 2:
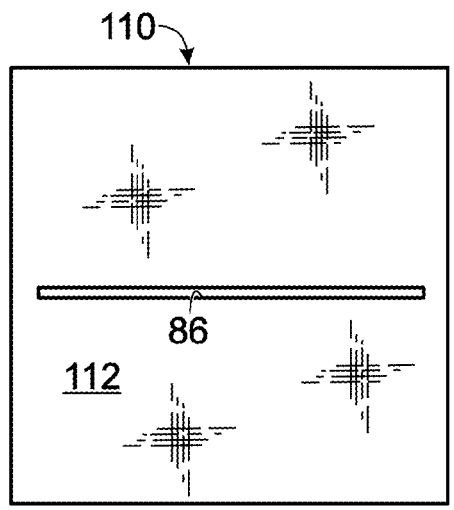
FIG. 2 is a view of a slit-forming optical element of the detection system of FIG. 1, taken generally along line 2-2 of FIG. 1.

FIG. 2 shows a slit-forming optical element 110 of detection system 50 that creates optical slit 86. The slit is transparent for the optical radiation of the system, while an opaque body 112 around the slit prevents transmission of the optical radiation through optical element 110 elsewhere. Slit 86 may, for example, be created by an opening (an air gap) in body 112 or as an unmasked area on an otherwise masked surface of body 112. The slit is elongated orthogonal to optical path 77 followed by beam 76 at optical element 110, and elongated orthogonal to a direction of elongation of channel 60 (and fluid flow) through irradiation zone 66 (after correcting for a change in direction, if any, in the optical path between optical slit 86 and irradiation zone 66 (e.g., a change in direction created by a mirror)).

Figure 3:
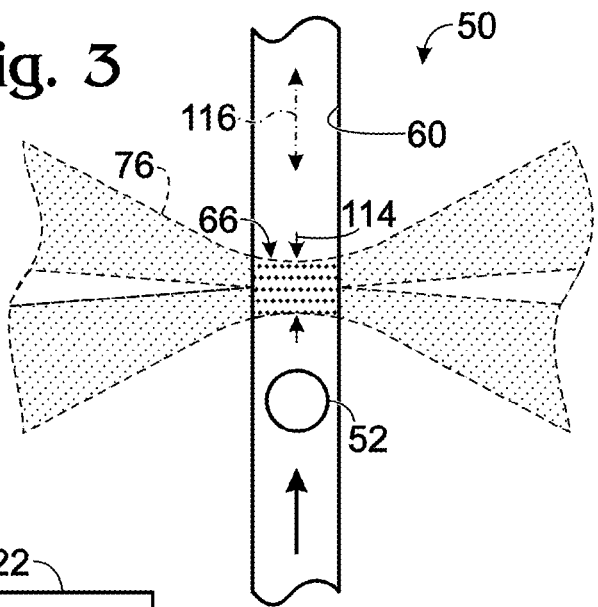
FIG. 3 is a fragmentary view of the detection system of FIG. 1, taken where a light beam intersects a flow channel to create an irradiation zone, also called a detection volume.

FIG. 3 shows irradiation zone 66 of channel 60 in more detail. Optical elements located in the optical path between slit 86 and channel 60 may collimate beam 76 and then focus the beam 76 on a section of the channel. The channel may be elongated in an image plane of slit 86 (see FIG. 1), such that the slit is projected onto the section of the channel to create a volume within the channel that is irradiated by beam 76. This volume, which is stippled distinctly in FIG. 3, is equivalent to irradiation zone 66, and may be described as a detection volume because the changing contents of this volume, as carrier fluid and particles flow through channel 60, may be a primary determinant of how much light is sensed by each detector over time.

The width of slit 86 and the magnification or minification, if any, created by optical elements between the slit and irradiation zone 66, define a projected width 114 of the slit in channel 60. Projected slit width 114, measured parallel to a long axis 116 of the channel, determines the size of irradiation zone 66 within the channel. For example, if slit 86 has a width of 35 µm, and the optical subsystem has a magnification of two between slit 86 and channel 60, projected width 114 is 70 µm. Accordingly, the width of slit 86 may, for example, be selected according to the diameter (or length) of particles 52 being detected, such that projected slit width 114 is less than the diameter (or length) of particles 52. In exemplary embodiments, the projected slit width is about 40-90%, 50-80%, or 60-70% of the particle diameter (or length). The length of the particles is defined in channel 60 as each particle passes through the irradiation zone.

Figure 4:
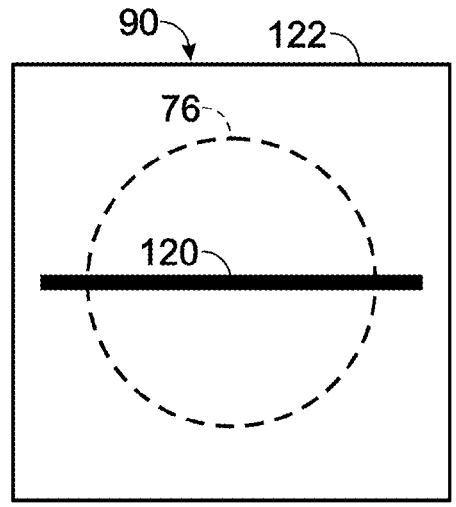
FIG. 4 is a view of a mask of the detection system of FIG. 1, taken generally along line 4-4 of FIG. 1.

FIG. 4 shows mask 90 of detection system 50. The mask may block any suitable transverse portion of the beam. For example, the mask may be a line mask that provides a narrow, elongated, non-transmissive region, namely, a line 120 to block a portion of beam 76. Line 120 may be oriented parallel to optical slit 86, and may or may not be centered on beam 76 and/or optical axis 78. The mask may, for example, be formed by a transparent substrate 122 having an opaque coating to create an opaque line 120. For example, substrate 122 may be formed of glass, and line 120 may be produced by chromium etching of an elongated surface region of the glass. The mask may be considered to be the entire optical element or only an opaque region thereof. In some examples, the line mask may be created by a discrete elongated member, such as a thin wire. In some examples, the mask may have a different shape of masking element, such as a non-elongated shape (e.g., a circle or square) to create a point mask.

Line 120 may have any suitable size and position. The line may be longer than the diameter of beam 76, as shown in FIG. 4. The width of line 120 may be substantially less than the beam's diameter, such as less than about 20%, 10%, or 5%, among others, of the diameter. The line may block any suitable portion of the beam's cross-sectional area (and/or light), such as less than about 10%, 5%, or 2%, among others. Exemplary widths of line 120 include less than about 1 mm, 700 µm, or 400 µm, among others.

Figure 5:
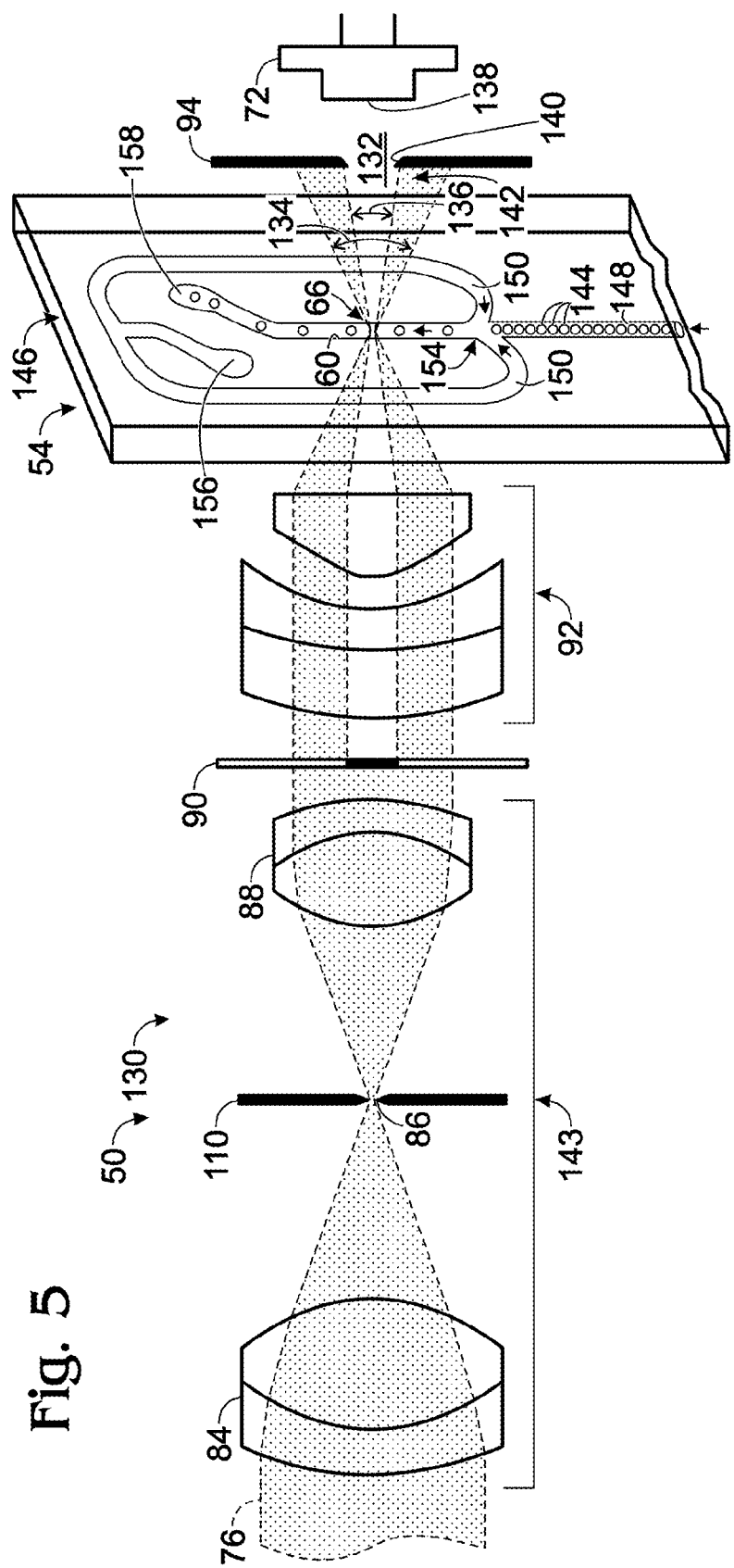
FIG. 5 is a fragmentary, schematic view of an embodiment of the detection system of FIG. 1, with the beam of light stippled to illustrate how a mask forms a shadow region in the beam, in accordance with aspects of the present disclosure.

FIG. 5 shows an embodiment 130 of detection system 50. Beam 76 is stippled to illustrate how mask 90 blocks a portion of the beam to form a shadow region 132 (interchangeably termed a dark region) in the beam. Portions of the shadow region may be located optically upstream and downstream of the irradiation zone (and channel 60). However, in the depicted embodiment, the downstream portion provides a location for detection of deflected light. The shadow region may represent any suitable portion of a beam angle 134 defined by a diverging region of the beam extending away from channel 60 toward deflection detector 72. For example, the shadow region may define a shadow region angle 136 of less than about 8, 6, 5, 4, 3, or 2 degrees, among others.

Deflection detector 72 has a photosensitive area 138 that is aligned with shadow region 132. An optical slit 140 defined by optical element 94 is sized and positioned to prevent undeflected light 142 of beam 76 from striking photosensitive area 138. In other words, optical slit 140 may be narrower than the width of shadow region 132 where the beam strikes optical element 94. Optical slit 140 may be located in the image plane of mask 90. Deflection detector 72 is positioned behind (downstream from) optical element 94 and its slit 140 and detects light from beam 76 that is deflected into the shadow region. A suitable position for slit 140 and/or deflection detector 72 may be determined by the proximity of mask 90 to the back focal plane of objective 92. If the mask is placed in this focal plane, the image plane for the mask is located at infinity behind channel 60. Accordingly, the mask can be positioned with an offset from the back focal plane to move the mask's image plane to a convenient distance from channel 60. Photosensitive area 138 of detector 72 may be positioned near the image plane of the mask, such as close to and directly behind slit 140. Alternatively, or in addition, light that has passed through the irradiation zone, and particularly deflected light, can be focused with an optical element, as described below in Example 1.

In order to achieve a high signal-to-noise ratio, the slit may be located in the mask's image plane. Moving the slit closer to or farther from the objective, and therefore out of the image plane, rapidly reduces contrast of the mask image and increases noise. The contrast is reduced because the slit has a finite width, and the light coming though it may not be perfectly collimated when incident on the mask. An idealized, masked beam pattern (i.e., a sharp mask shadow at any downstream position), shown in FIG. 1, only may occur for a mask inserted in a perfectly collimated beam.

A mask image formed in an image plane of mask may or may not be magnified or minified with respect to the physical mask. In the depicted embodiment, the image of the mask is minified 0.5× relative to the physical mask. For example, if a line of the physical mask has a width of 300 µm, the width of the line in the mask image may be 150 µm.

Detection system 130 illustrates additional exemplary aspects of system 50 of FIG. 1. For example, system 130 incorporates an objective 92 formed by two or more lenses, which may be pre-assembled with one another to create a unit. In the depicted embodiment, the objective is a Meiji objective having 40× magnification, a numerical aperture of 0.6, and a working distance of 2.8 mm. A spatial filter 143 providing a 2× magnification is formed by lenses 84 and 88, and slit-forming optical element 110. Also, fluidics subsystem 54 is designed to transport droplets 144 (as particles 52) through irradiation zone 66 in a channel-forming member 146 that is planar. The droplets are disposed in an immiscible carrier liquid 148 (e.g., oil). The separation, if any, between droplets approaching irradiation zone 66 may be increased by introduction of additional carrier fluid 150 from one or more dilution channels at a channel junction 154 that is fluidically upstream of irradiation zone 66. Channel member 146 also may have an inlet 156 for ingress of additional carrier fluid and an outlet 158 for egress of droplets 144 after passing through the irradiation zone.

Figure 6:
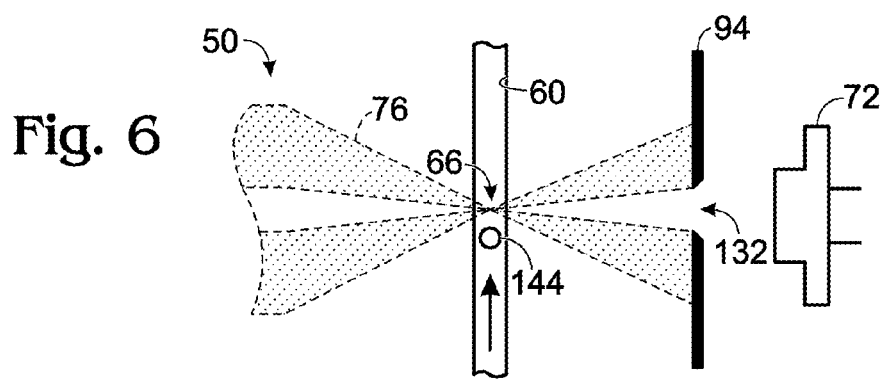
FIGS. 6-9 are a temporal series of fragmentary views of the detection system of FIG. 1, taken as a particle (e.g., a droplet) passes through the detection volume of the system and illustrating how incident light may be deflected by different regions of the particle, in accordance with aspects of the present disclosure.
Figure 7:
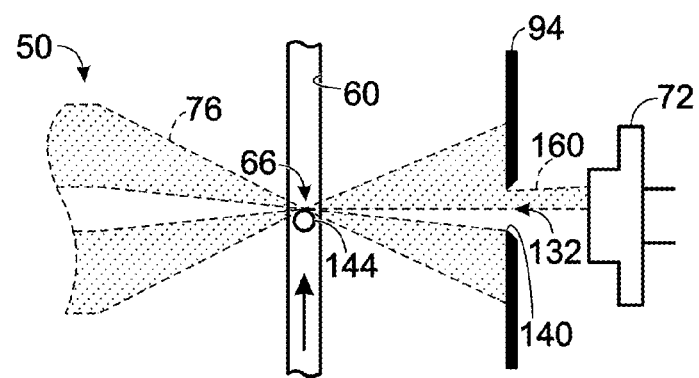
Figure 8:
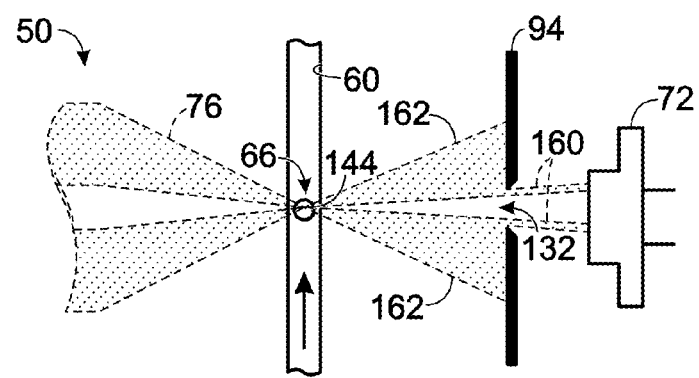
Figure 9:
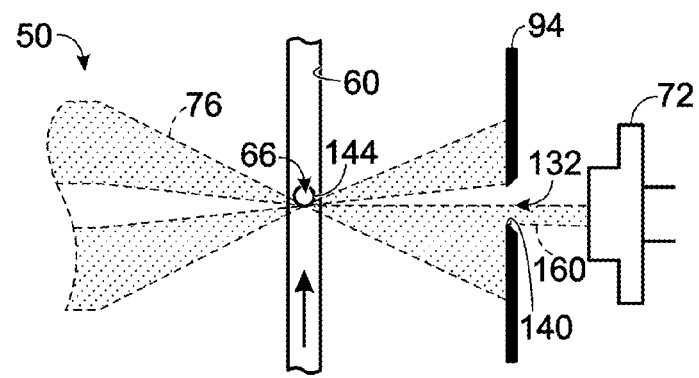

FIGS. 6-9 show exemplary deflection of light within detection system 50 as a particle (e.g., a droplet 144) passes through irradiation zone 66. In FIG. 6, the entire droplet is outside of irradiation zone 66. No deflected light reaches deflection detector 72. In FIG. 7, a leading edge of the droplet has entered the irradiation zone, which produces deflected light 160 that enters shadow region 132 sufficiently to pass through optical slit 140 and reach detector 72. In FIG. 8, the droplet is roughly centered in the irradiation zone and produces deflected light 160 that enters shadow region 132 from both branches 162 of beam 76. (Each branch 162, also called a beam portion, may have about the same intensity if the line mask is centered on the beam.) In FIG. 9, the trailing edge of the droplet has entered the irradiation zone, producing deflected light 160 that enters shadow region 132 sufficiently to pass through optical slit 140 and reach detector 72.

Further aspects of exemplary assays with, and detection systems for, droplets are described in U.S. Patent Application Publication No. 2010/0173394 A1, published Jul. 8, 2010, which is incorporated herein by reference.

II. FLUIDICS SUBSYSTEM

This section describes exemplary aspects of the fluidics subsystem and exemplary carrier fluid and particles therein.

The fluidics subsystem includes at least one channel 60 to contain and direct movement of carrier fluid and particles. The channel may have any suitable cross-sectional shape, such as circular, elliptical, polygonal, or the like. The channel may have a cross-sectional dimension that is approximately the same as or greater than the diameter of the particles. In exemplary embodiments, the channel is a microfluidic channel, namely, a channel having a cross-sectional dimension less than about 1 mm. Exemplary channels have a length that is at least about 2, 5, 10, or 20 times the minimum cross-sectional dimension of the channel. The channel may be a circumferentially-enclosed passage defined in a planar member, or may be an enclosed passage defined inside a tube (e.g., a tube with a cylindrical exterior), among others. The channel may be formed at least in part by molding, wet etching, dry etching, laser etching, machining, or the like.

The fluidics subsystem may include a source of negative pressure (a vacuum) to pull fluid along the channel, positive pressure to push fluid along the channel, or both. In either or both cases, the pressure may be created by a pump. The pump may be a positive-displacement pump, such as a syringe pump, among others. Other exemplary pumps include peristaltic pumps, rotary pumps, or the like. In other examples, the pressure may be provided by a container introduced to the system while holding pressurized gas or a vacuum.

The carrier fluid may be any suitable liquid or gas phase capable of transporting the particles along the channel. The carrier fluid and the particles both may be liquid, for example, a dispersed liquid phase encapsulated by a continuous liquid phase, as in an emulsion. Accordingly, the carrier phase may include oil, and optionally a surfactant. Suitable oils may include a fluorine-containing oil, a silicone oil, or mineral oil, or any combination thereof, among others. In other embodiments, the carrier phase may be a gas phase or a liquid phase and the particles may be solid-phase objects, the carrier phase may be a gas phase and the particles may be droplets (e.g., as an aerosol), or the carrier phase may be a liquid phase (e.g., an aqueous phase) or a gas phase and the particles may be biological cells.

Particles detected by the detection system of the present disclosure may exist in any suitable phase, such as a liquid phase, a solid phase, or a combination thereof, among others. Exemplary particles include droplets, beads or other small solid-phase objects, biological cells, and the like.

Particles may have any suitable size. Generally, particles are less than about 1 mm in diameter and/or less than about 1 µL in volume. The particles may be at least about 1 µm in diameter and/or at least about 1 fL in volume.

Particles may have any suitable shape. Exemplary shapes include spherical, cylindrical, bullet-shaped, irregular, random, or the like. Droplets and other particles may have a size and/or shape sensitive to one or more parameters of the fluidics subsystem. The diameter and/or shape of the droplets may be influenced by the diameter of channel 60. The shape of the droplets may be spherical, and the droplets may have a diameter that is less than the diameter of channel 60. In other cases, the droplets may be elongated, with a diameter corresponding to the channel's diameter. The shape of the droplets also may be affected by the flow rate of the carrier fluid, which may determine how much the droplets are stretched or otherwise deformed as they pass through the irradiation zone. In some embodiments, the droplets may have a surface layer that discourages deformation of the droplets, such that the droplets are relatively insensitive to deformation by the fluidics subsystem.

The particles may be photoluminescent, namely, capable of emitting light when irradiated with excitation light of the appropriate wavelength. Exemplary types of photoluminescence include fluorescence, phosphorescence, and the like. Each particle may contain a photoluminophore, which is any atom, molecule, moiety, complex, or aggregate capable of photoluminescence. Suitable photoluminophores include fluorescent dyes, quantum dots, and the like.

III. OPTICAL SUBSYSTEM

This section describes further aspects of the optical subsystem.

The optical subsystem may incorporate any suitable number of light sources, such as 1, 2, 3, 4, or more. The light sources may be operated to produce optical radiation that reaches the irradiation zone at the same time or at different times (e.g., alternately or sequentially).

Each light source may generate optical radiation of any suitable wavelength. In some embodiments, each light source or at least two light sources may emit visible light (e.g., at a different wavelength from other light sources of the system), or at least two light sources may emit different types of optical radiation (e.g., one light source may emit ultraviolet radiation and another light source may emit visible light).

The light source may incorporate at least one light-emitting element to generate light, and, optionally, one or more optical elements to collect and/or focus the generated light to form a beam. Exemplary light sources and/or light-emitting elements include electroluminescent lamps (e.g., light-emitting diodes and lasers (such as laser diodes)), high-intensity discharge lamps (e.g., a mercury arc lamp), and the like. Light-emitting diodes (LEDs) include any solid-state device that generates light by electroluminescence, including semiconductor LEDs, organic LEDs, and/or polymer LEDs, among others.

Each detector, also called an optical detector or photodetector, may include at least one photosensor configured to detect light of any suitable wavelength. The detector may be a point detector (e.g., a photodiode or photomultiplier) or an image detector, among others. Exemplary image detectors include multi-pixel photon counters (MPCC) (e.g., silicon photomultipliers (SiPM)), charge-coupled device (CCD) sensors, active pixel sensors (e.g., complementary metal-oxide-semiconductor (CMOS) sensors, N-type metal-oxide-semiconductor (NMOS) sensors, etc.), or the like. The detector detects light and creates a signal (e.g., an electrical signal) representing the detected light. The detector may convert photons into electrical current or voltage.

IV. METHODS OF PARTICLE DETECTION

The optical system disclosed herein may be utilized to perform a method of detecting a particle. The method steps presented in the section may be performed in any suitable order and combination, and may be modified by any other features and aspects of the present disclosure.

A beam of light may be generated. The beam may be generated with at least one light source and may, for example, contain visible light, optionally at least predominantly. In some embodiments, optical radiation of the light beam may be generated with at least one light-emitting diode or at least one laser.

The beam may be directed to a channel to create an irradiation zone in the channel where the beam intersects the channel. The channel may contain a carrier fluid flowing along the channel through the irradiation zone, with one or more particles disposed in the carrier fluid. Flow of the carrier fluid may move each of the particles through the irradiation zone, optionally serially. The flow of the carrier fluid may be driven by a pressure differential, which may be created by a pump.

The beam may be spatially filtered upstream of the channel. Spatial filtering may be performed at least in part in a focal plane of an optical element(s) of the system. The size of the beam may be restricted by spatial filtering, optionally with an elongated slit, such as an air slit, through which light of the beam passes. The slit may be arranged orthogonal to the channel (as defined by the long axis of the channel at and around the irradiation zone). The beam may be collimated upstream of the slit and focused on the slit. The beam may be collimated again at a position downstream of the site at which the beam is spatially filtered and upstream of the channel.

A transverse portion of the beam may be blocked upstream of the irradiation zone to create a shadow region. The shadow region may be created downstream of the region at which the beam is blocked. A mask may be used to create the shadow region. The mask may be disposed in a collimated region of the beam to block the portion of the beam.

The beam may be focused on the irradiation zone in the channel using an objective composed of one or more optical elements. Focusing the beam may be performed on a partially blocked region of the beam created by blocking the beam.

Light of the beam may be deflected by interaction with matter in the irradiation zone. The light may be deflected by a particle passing through the irradiation zone. The light may be deflected into the shadow region, and may be detected downstream of the irradiation zone. The particle passing through the irradiation zone may produce a temporary increase (a pulse) in the intensity of light detected in the shadow zone by a detector. The beam may be spatially filtered downstream of the channel, and upstream of the detector, with an optical slit operatively disposed in an optical path between the channel and the detector.

Photoluminescence induced by the beam at the irradiation zone may be detected. The detection of photoluminescence may be epi-fluorescence in which excitation light and emitted light share an optical path followed in respective opposite directions to and from the irradiation zone.

V. EXAMPLES

The following examples describe selected aspects and embodiments of the present disclosure related to optical detection of particles. These examples are included for illustration and are not intended to limit or define the entire scope of the present disclosure.

Example 1. Detection Configurations for Deflected Light

This example describes exemplary configurations for detecting deflected light in detection system 50 with deflection detector 72, with or without one or more optical elements located between irradiation zone 66 and the detector; see FIGS. 10-15. Each of the configurations of this example may be incorporated into any of the detection systems of the present disclosure.

Light may be deflected at the irradiation zone by various mechanisms including refraction, reflection, Mie scattering, and the like. The relative contribution of each mechanism may be determined by particle size, shape, composition, etc.; carrier fluid properties; the nature of the interface between each particle and the carrier fluid; and the like. For example, in some embodiments of droplets disposed in a carrier fluid comprising oil, small angle deflection by micelles and large molecules (e.g., proteins) inside a droplet and on its surface, and light refraction and multiple reflection at the interface between the droplet and the oil, all may deflect optical radiation into the shadow region. However, the latter effects (refraction and multiple reflection) may deflect incident optical radiation by greater angles, to produce "large angle" deflection. In any event, the detection system may be configured to detect deflected light of interest from only a portion of the shadow region, to selectively include and exclude deflected light according to the deflection angle. Large angle deflection may create a uniform intensity distribution of light across the slit while small angle deflection may bleed around the slit edges. Accordingly, when small angle deflection is more informative about the particles, a portion of the large angle deflection that is located more central to the shadow region can be selectively excluded. Alternatively, small angle deflection closer to the edges of the shadow region can be selectively excluded when large angle deflection is more informative about the particles. With this approach, the background level of the deflection signal may be reduced to increase the sensitivity of the detection system.

Figure 10:
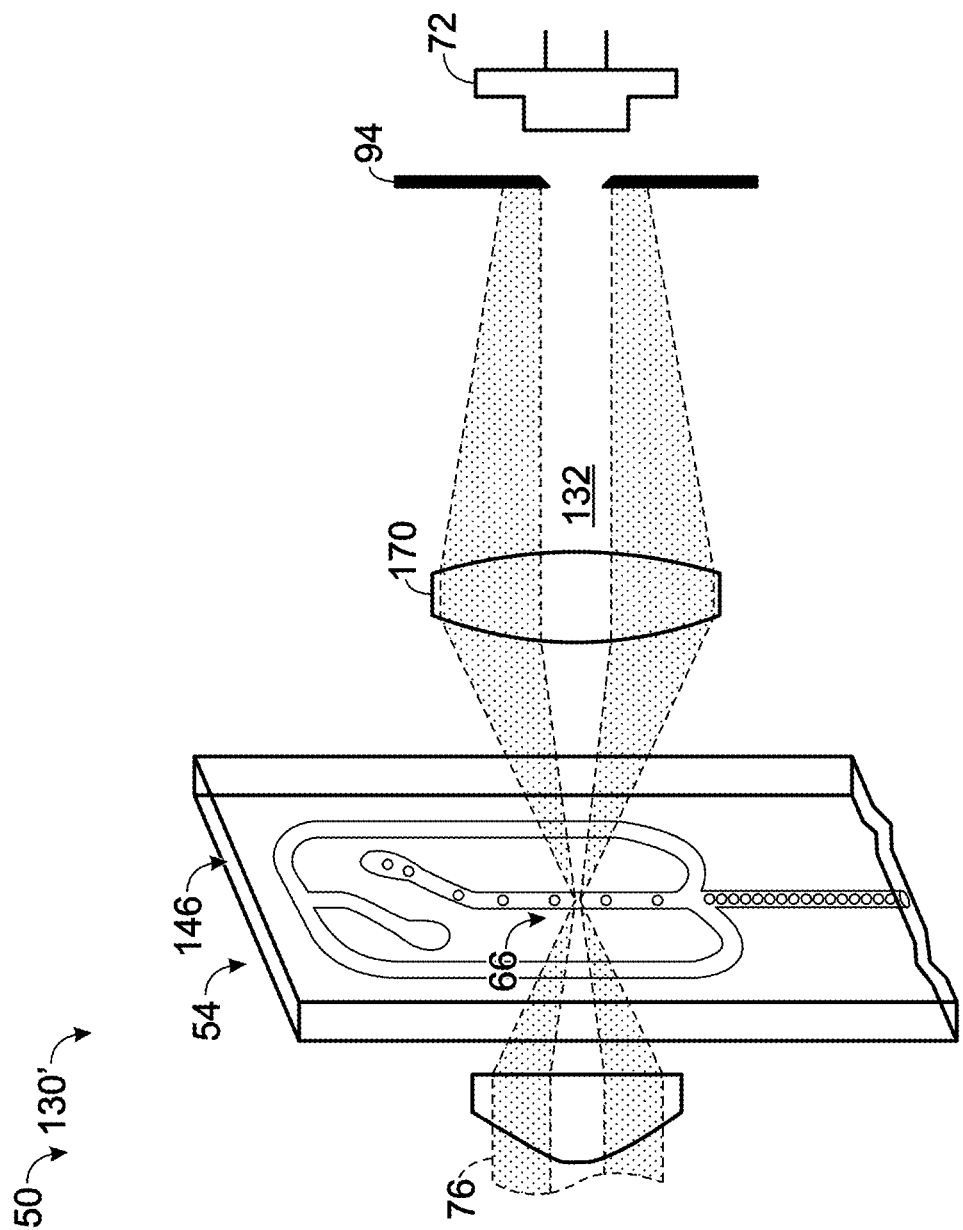
FIG. 10 is a modified version of the detection system of FIG. 4 created by addition of a relay lens to focus deflected light and move an image plane of the mask farther from the channel, in accordance with aspects of the present disclosure.

FIG. 10 shows a modified version 130' of detection system 130 of FIG. 5. System 130' adds a relay lens 170 between irradiation zone 66 and deflection detector 72. The relay lens may be located in a focal plane of mask 90 and re-images mask 90 to a greater distance from the irradiation zone (also see FIG. 5). Accordingly, slit-forming element 94 is located in an image plane of the mask at a position farther from the irradiation zone, which may be more convenient if space within system 50 near the irradiation zone is limited, and may increase contrast between the dark image of the mask and the area illuminated adjacent the image by beam 76. In some embodiments, the aperture of relay lens 170 may be reduced to exclude the beam and, optionally, deflected light near opposite edges of the shadow region, to selectively exclude light deflected by only a small angle. Alternatively, the aperture of relay lens 170 may be increased such that a greater amount of large angle deflection is detected, optionally predominantly. In some embodiments, the relay lens may have an aperture that renders slit-forming element 94 unnecessary.

FIG. 11 shows a fragmentary view of detection system 50 of FIG. 1, taken around flow channel 60 and deflection detector 72. The configuration of FIG. 11 is presented here as a reference for comparison to the modified configurations of FIGS. 12-15.

FIG. 12 shows a modified version 50a of the detection system of FIG. 1 with reduced detection of small angle deflection. System 50a has a slit-forming element 94a at the same position along the optical path as element 94 of system 50, namely, in the image plane of mask 90 (see FIG. 1), but defines a narrower optical slit 140a. Accordingly, the width of the slit may be adjusted to reduce background.

FIG. 13 shows yet another modified version 50b of detection system 50. System 50b replaces detector 72 with a detector 72b having a smaller photosensitive area 138b. Area 138b may be located in the image plane of mask 90 (see FIG. 1), in place of optical slit 140 (compare with FIG. 11). The photosensitive area may be sized and positioned such that no portion of beam 76 is incident on area 138b (or detected). Instead, only light deflected in irradiation zone 66 can reach area 138b and be detected. The size and aspect ratio of area 138b may be selected to at least generally match that of the shadow region in the image plane of the mask. For example, area 138b may be elongated parallel to optical slit 86 and/or parallel to a line of mask 90. Area 138b may have an aspect ratio of at least about 5:1, or 10:1, among others. The width of area 138b may be selected to include or exclude small angle deflection.

FIG. 14 shows still another modified version 50c of detection system 50. System 50c is created from system 50 by replacement of downstream optical slit 140 with a slit-forming element 94c having a pair of optical slits 140c that are parallel to one another. The pair of optical slits each may be located in the image plane of mask 90 (see FIG. 1) and may be separated by a masking region 180. Masking region 180 reduces detection of large angle deflection. Alternatively, or in addition, another optical slit may be disposed between optical slit 140 of FIG. 11 and detector 72.

FIG. 15 shows yet still another modified version 50d of detection system 50. A mask 190 is attached to the deflection detector and covers portions of photosensitive area 138. Mask 190 may be located out of the mask's image plane. Accordingly, there may be no good correlation between a point on area 138 and the deflection angle of light that can reach that point. However, extra masking or baffling of detector 72 may be effective to control some undesired light that could be present due to light deflection that occurs outside of the detection volume, for example, from an outer surface region of a channel-forming member or various imperfections.

Example 2. Intensity Distributions

Figure 16:
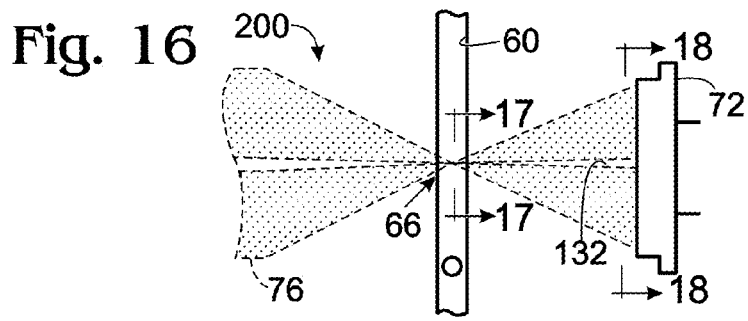
FIG. 16 is a fragmentary view of an embodiment of the detection system of FIG. 1 configured to detect deflected light and undeflected light at a position downstream of the irradiation zone of the channel.
Figure 17:
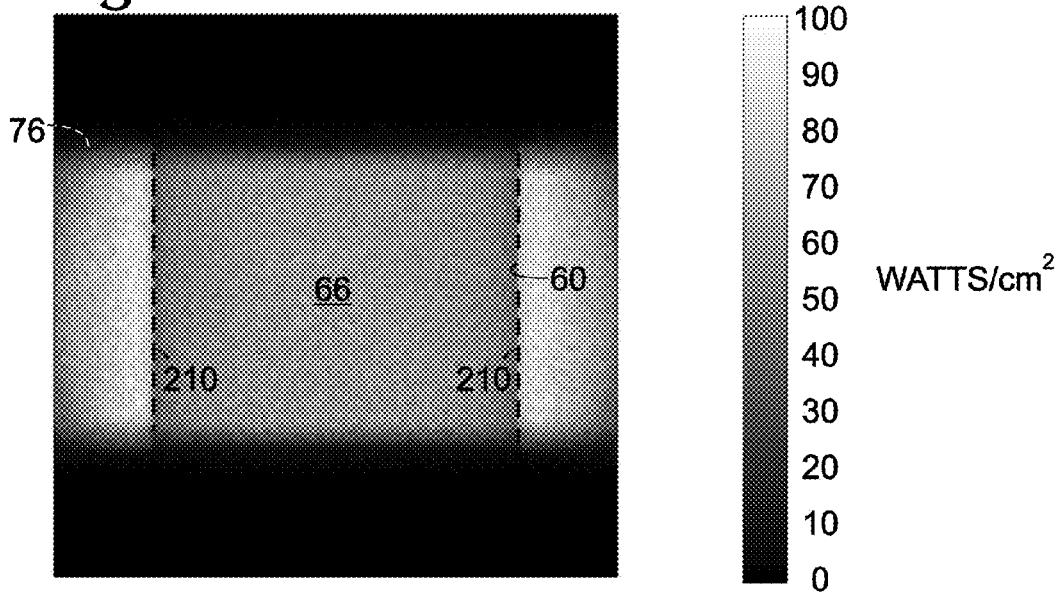
FIG. 17 is a calculated intensity distribution of light within the detection system of FIG. 16 for a region indicated generally by line 17-17 in FIG. 16 and located in and around the irradiation zone.
Figure 18:
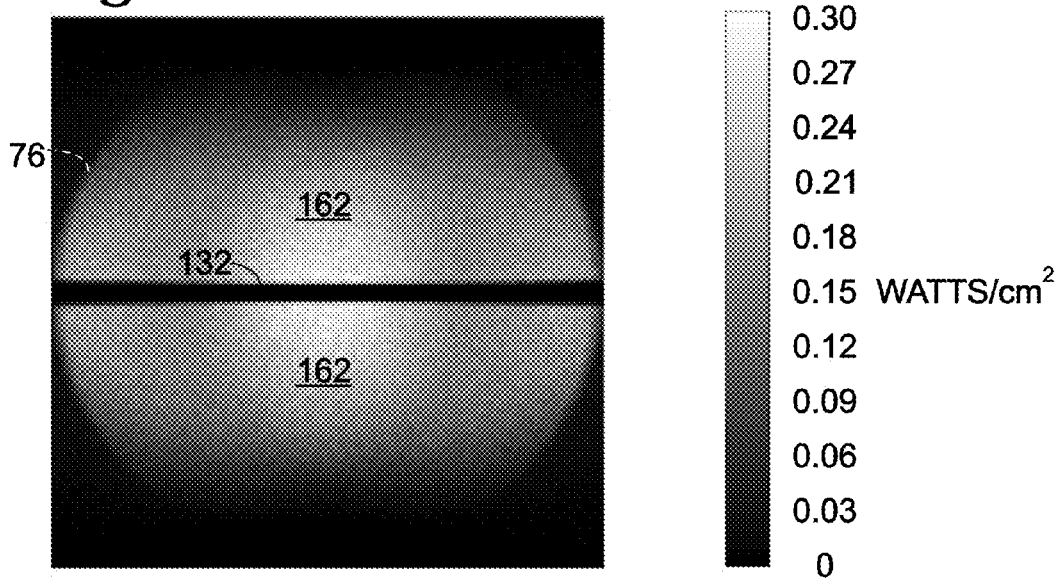
FIG. 18 is a calculated intensity distribution of light incident on a detector of the system of FIG. 16 at the region indicated generally by line 18-18 in FIG. 16.

This example describes intensity distributions calculated with optical modeling software for an exemplary detection system 200; see FIGS. 16-18.

FIG. 16 shows detection system 200 having a deflection detector 72 sized and positioned to be illuminated by the full cross-section of beam 76. Detector 72 may be an imaging detector configured to detect beam 76 and shadow region 132. Light deflected into the shadow region may be detected as an increased intensity for image pixels representing the shadow region.

FIG. 17 shows a calculated intensity distribution of light in irradiation zone 66 of detection system 200, in a plane orthogonal to the optical path of the beam and bisecting the irradiation zone. The intensity distribution was calculated with Zemax® software for a 100×100 μm region of the plane. Irradiance levels within the image are defined by the scale to the right of the image. Opposite wall regions 210 of channel 60, which delineate part of the irradiation zone, are indicated with dashed lines.

FIG. 18 shows a calculated intensity distribution of light detected by detector 72 of detection system 200. The intensity distribution was calculated with Zemax® software for a 2×2 mm square region of the detector. Irradiance values within the image are defined by the scale to the right of the image. Beam 76, shadow region 132, and separate beam portions (branches 162) of the beam are indicated.

Example 3. Detection System Embodiment

Figure 19:
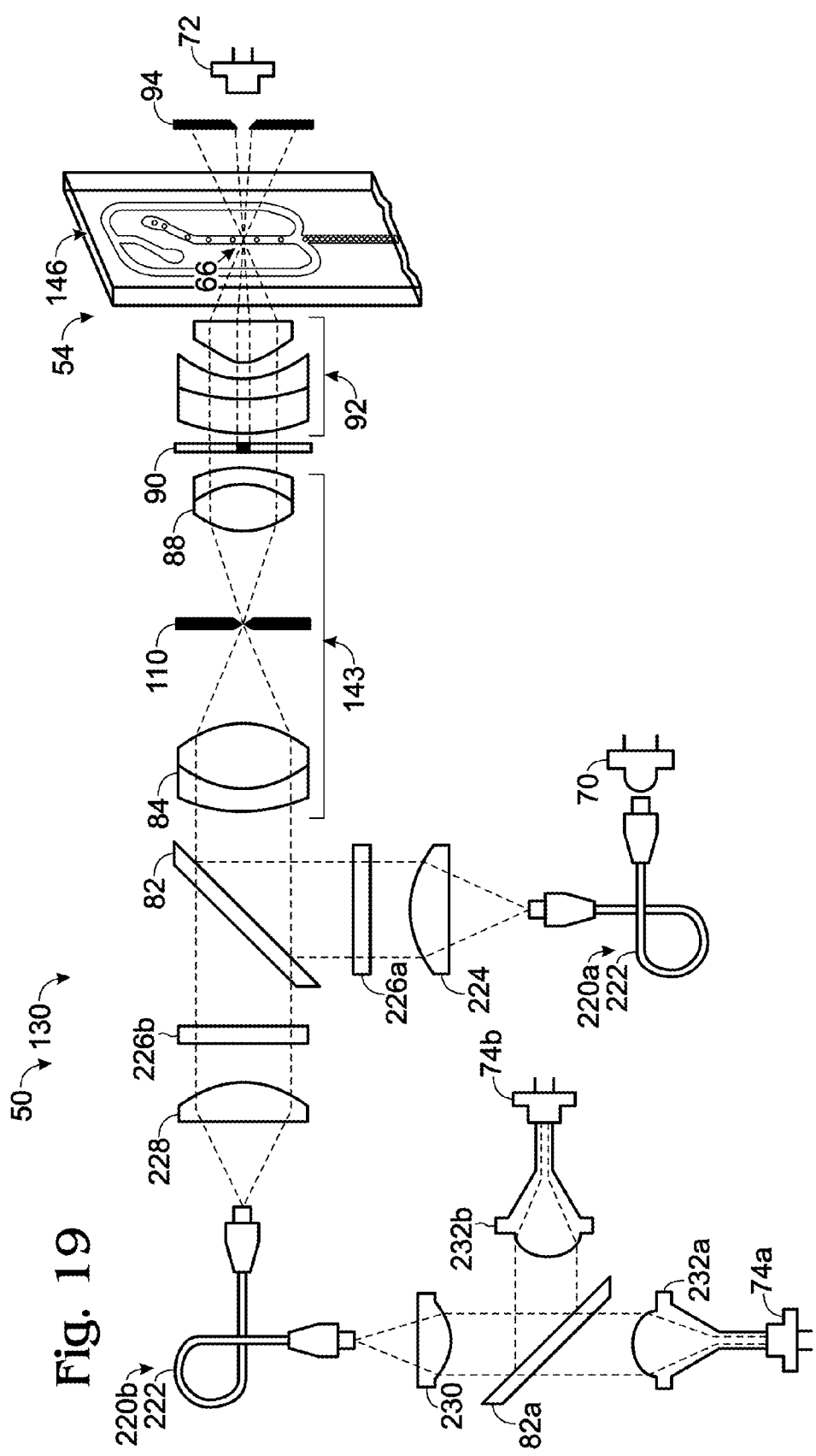
FIG. 19 is a more complete view of the detection system of FIG. 5, with the view including a light source and a pair of photoluminescence detectors.

This example describes further aspects of detection system 130; see FIG. 19 (also see FIG. 5).

Detection system 130 has a light source 70 (e.g., an LED) and a pair of photoluminescence detectors 74a, 74b each optically coupled to spatial filter 143 and objective 92, in part, by a light guide 220a or 220b. Each of the light guides includes an optical fiber 222 that allows the optical paths for excitation and emission to bend, as needed.

Excitation light produced by light source 70 passes, in order, through light guide 220a, a collimating lens 224, and a spectral filter 226a. The excitation light then is reflected toward spatial filter 143 by a beam splitter 82 (here, a long-pass mirror), and propagated through objective 92 and irradiation zone 66, for excitation of a photoluminophore(s) therein and deflection.

Light emitted from irradiation zone 66, as photoluminescence induced by the excitation light, travels in reverse through objective 92, spatial filter 143, beam splitter 82, a spectral filter 226b, a focusing lens 228, light guide 220b, and a collimating lens 230. A portion of the collimated, emitted light then passes through a beam splitter 82a to a focusing light guide 232a and detector 74a. Another portion of the collimated, emitted light is reflected by beam splitter 82a to focusing light guide 232b and detector 74b.

Detection system 130 may incorporate one or more additional light sources and/or one or more additional photoluminescence detectors. Accordingly, the detection system may be configured to detect photoluminescence in only one channel with one detector, at least two channels with two detectors (as shown in FIG. 19), or three or more channels with three or more detectors, among others.

Example 4. Exemplary Deflection and Photoluminescence Data

Figure 20:
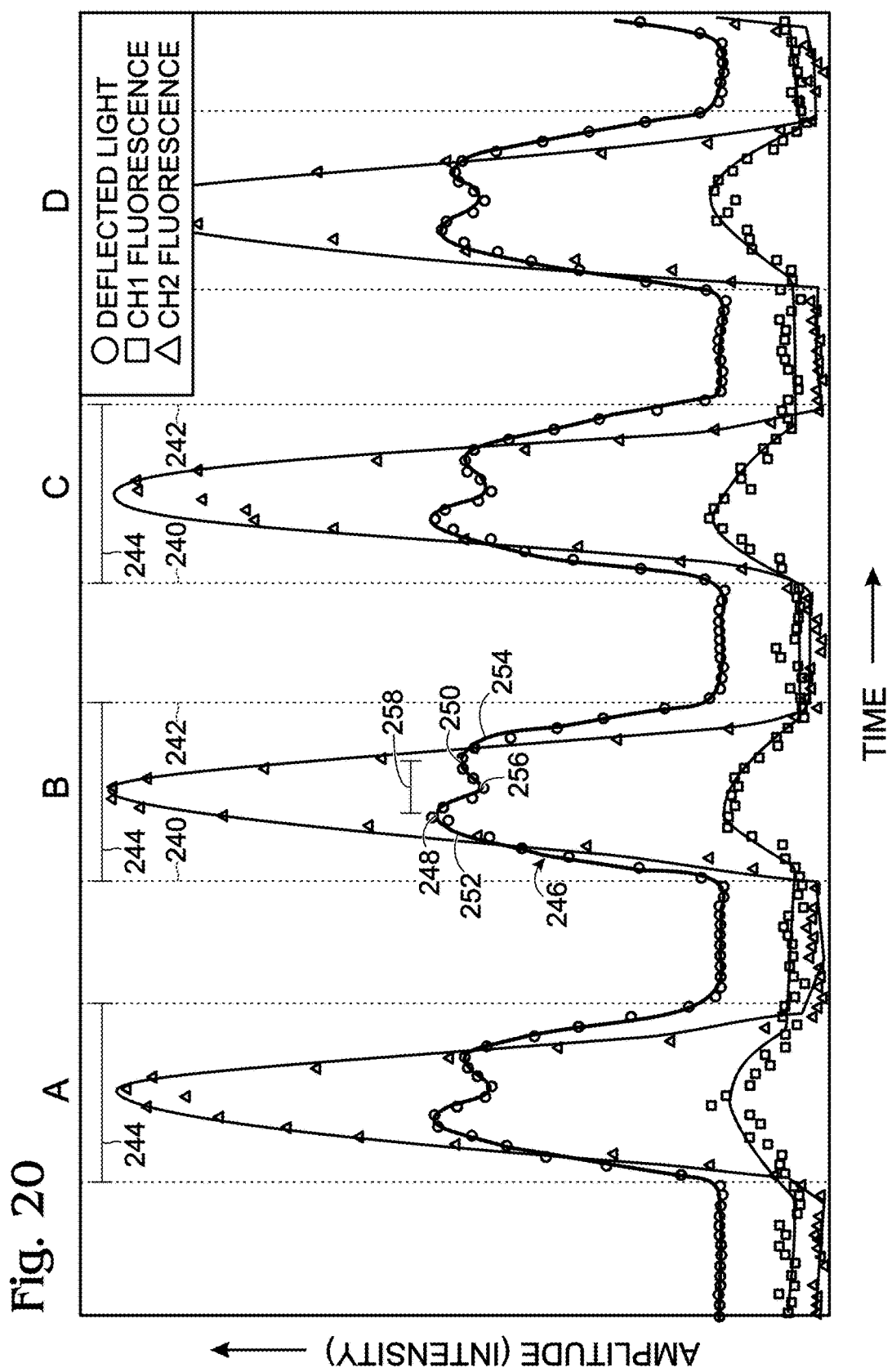
FIG. 20 is a graph of the intensity of deflected light and fluorescence detected with a working model of the detection system of FIG. 19, as a function of time from a series of droplets traveling through the irradiation zone of a channel.

This example describes exemplary deflection and photoluminescence data collected from droplets with a working model of detection system 130; see FIG. 20.

Droplets containing a pair of fluorescent dyes were generated. The dyes emit light that is detectable with detectors 74a and 74b, respectively (see FIG. 19). The signals registered by detectors 74a and 74b are designated as channel 1 (CH1) and channel 2 (CH2) fluorescence, respectively, in FIG. 20. A deflection signal was detected by detector 72 synchronously with detection of the signals of the two fluorescence channels by detectors 74a and 74b. The intensity of each signal was plotted as a function of time as four droplets were passed through the irradiation zone. Portions of the signals representing the four well-separated droplets are indicated by the letters A, B, C, and D, in FIG. 20.

FIG. 20 shows the deflection signal rising from baseline as the leading edge of each droplet enters the irradiation zone, indicated by a dashed line at 240, and returning to baseline upon exit of the trailing edge of the droplet from the irradiation zone, indicated by a dashed line at 242, to define a transit interval or span 244 for the droplet. Variations in the deflection signal caused by the droplet during the transit interval create a droplet waveform 246. The waveform includes at least one peak (i.e., a local maximum) and may, as shown, include a leading peak 248 (a first local maximum (a first height)) and a trailing peak 250 (a second local maximum (a second height)) to form a double peak (two local maxima). The waveform may have a signature characteristic of a droplet or other particle. Peaks 248, 250 may be created by corresponding leading and trailing regions of the droplet (and corresponding waveform), particularly a pair of humps 252, 254 formed by the leading and trailing regions of the droplet. The humps may create a valley 256 (a local minimum) located temporally intermediate the pair of peaks. Any suitable characterizing value(s) calculated from the waveform and/or features thereof may contribute to analysis of droplet size, droplet shape, and/or flow velocity of fluid through the irradiation zone. The characterizing values of a waveform may include the width/time interval of the waveform measured at baseline, and/or at one-half the maximum amplitude or waveform height, among others. The characterizing values also or alternatively may include a separation value 258 corresponding to a temporal separation between the peaks within the waveform, or the like. The characterizing values also or alternatively may include a relative size (height and/or width) of the leading and trailing regions of the waveform relative to one another, a ratio of a peak or waveform height and the local minimum between peaks, a period between waveforms, and/or the like.

Example 5. Further Aspects of Particle Detection Systems

This example describes further exemplary aspects of particle detection systems.

The detection system may be based on focused light of any detectable wavelength being deflected by a particle, such as a droplet, while the particle is in the detection volume. For the case of optically transparent particles, at least three mechanisms (e.g., Mie scattering, refraction, and reflection) can come into play. The detection of deflected light may be accompanied with measuring the fluorescence intensity originating from dye molecules inside particles, such as droplets. The same light source may be used to generate deflection and fluorescence signals, and thus optical radiation from the light source may be referred to as excitation light. Processing of synchronously-acquired deflection and fluorescence signals increases the accuracy of the amplitude and span of the fluorescence signal of each particle, in particular for particles having only weak (or no) fluorescence.

The detection system is based on blocking a fraction of the collimated excitation light before it is focused by an objective into a detection volume. An air slit and the magnification produced by a collimating lens and a focusing objective may define a detection volume inside a flow channel. A line mask may be located at the back focal plane of the focusing objective or, when the back focal plane is inaccessible, as close to it as possible. Most large-magnification objectives have the back focal plane inside their bodies. Testing was performed with a line mask constituted by a thin, straight black wire. The wire was mounted to the back aperture of the focusing objective. The direction of the wire was aligned with the direction of the air slit. The focusing objective creates an image of the line mask at a certain distance behind the detection volume. The closer the line mask to the objective's back focal plane, the greater the distance between the detection volume and the line mask image; the image is created at infinity when the line mask is exactly at the objective back focal plane. Therefore, outward of the back side of the flow channel (i.e., to the right of channel 60 in FIG. 1), there exists a shadow region created by the line mask. Another air slit may block light outside of the shadow region, and a light detector may detect light intensity right behind the air slit.

The air slit in front of the deflection detector may be selected to have its width slightly narrower than the line mask image and its direction may be aligned with the direction of the line mask image. Thus, the deflection detector stays in darkness until a particle enters the detection volume. The presence of the particle changes the paths of light rays across the detection volume and some light reaches the deflection detector, creating a deflection signal.

The disclosed detection scheme is different from the layout of a forward scattering channel used in many flow cytometers. In the case of forward scattering, a narrow laser beam, focused with a relatively long focal length lens (e.g., 50-100 mm) into a flow channel, is entirely blocked with an opaque optical stop at the other side of the channel, while small angle scattered light is detected around the stop.

The detection system disclosed herein has various advantages over flow cytometers having a forward scattering channel. First, there may be no need to use a high quality laser beam, i.e., a beam that is both narrow and well-collimated. Instead, the optical detection system disclosed herein was tested with low-cost, high-power LEDs coupled to multimode optical fibers, as well as with diode lasers coupled to the same multimode optical fibers, and demonstrated comparable performance with the different light sources. In fact, any light source that can be coupled into a large-core optical fiber and then collimated may be suitable for the detection of deflected light, as described herein. Second, there may be no need to use a second objective to collect fluorescence. In many flow cytometry instruments, a separate high numerical aperture objective mounted at 90 degrees with respect to the excitation laser optical path collects light emitted by fluorescence. The focusing objective of the present disclosure may be configured to have a short working distance and high numerical aperture, which allows construction of an epi-fluorescence confocal layout, as shown in FIG. 1, where the same objective focuses the irradiation/excitation beam on the detection volume and collects light emitted by fluorescence. The registered fluorescence amplitudes shown in FIG. 20 were acquired in an epi-fluorescence confocal mode.

A black line mask at the main objective back aperture creates a shadow across the illuminated area at the opposite side of a flow chip (a planar member defining a flow channel). The shadow half angle is two degrees. A photodiode with an air slit in front of it normally stays in the shadow. Once a droplet enters the detection volume, the droplet deflects some of the excitation light, which passes through the slit and generates photocurrent. With a droplet-diameter-to-wavelength ratio around 100, Mie theory predicts negligible scattering at angles above two degrees, so the detection mechanism may be based on droplet "lensing" due to a lower refractive index of water (1.33) than silicone oil (1.39). The mask preferentially may be a long line due to a round flow channel serving as a negative power cylindrical lens, such that a round spot mask (a point mask) creates little shadow. The mask does not interfere with the image formation of a telescope's slit, i.e., the detection area is still a sharp, uniformly-illuminated line. Total light losses due to both excitation light and fluorescence being masked by the mask may stay below 5, 4, 3, or 2 percent, among others.

Example 6. Selected Embodiments

This example describes selected embodiments of the present disclosure as a series of indexed paragraphs. These embodiments should not limit the entire scope of the present disclosure.

Paragraph 1. A detection system for particles, comprising: (A) a channel; (B) a light source configured to generate light; (C) one or more optical elements configured to focus a beam of the light on an irradiation zone within the channel; (D) a mask operatively disposed in an optical path between the light source and the channel, wherein the mask is configured to block a portion of the beam, thereby producing a shadow region; and (E) a detector configured to detect light deflected from the beam into the shadow region by interaction with a particle passing through the irradiation zone.

Paragraph 2. The detection system of paragraph 1, wherein the irradiation zone is located in an optical path between the mask and the detector.

Paragraph 3. The detection system of paragraph 1 or paragraph 2, wherein the light source includes a light-emitting diode or a laser diode.

Paragraph 4. The detection system of any of paragraphs 1 to 3, wherein the mask is a line mask.

Paragraph 5. The detection system of any of paragraphs 1 to 4, wherein the mask intersects a collimated region of the beam.

Paragraph 6. The detection system of any of paragraphs 1 to 5, further comprising an optical slit operatively disposed in the optical path between the light source and the channel at a position optically upstream of the mask.

Paragraph 7. The detection system of paragraph 6, wherein the mask is a line mask including a masking region elongated parallel to the optical slit.

Paragraph 8. The detection system of paragraph 7, wherein the masking region is elongated orthogonal to a flow direction in the channel through the irradiation zone.

Paragraph 9. The detection system of any of paragraphs 6 to 8, wherein the optical slit is a first optical slit, further comprising a second optical slit operatively disposed in an optical path between the irradiation zone and the detector.

Paragraph 10. The detection system of any of paragraphs 1 to 9, wherein the detector is a first detector, further comprising a second detector configured to detect photoluminescence induced by the beam in the irradiation zone.

Paragraph 11. The detection system of paragraph 10, wherein the one or more optical elements provide an objective that collects emitted light from the irradiation zone for propagation to the second detector.

Paragraph 12. The detection system of paragraph 10 or paragraph 11, wherein the same light source generates (i) light deflected by the particle at the irradiation zone and detected by the first detector, and (ii) excitation light that induces photoluminescence in the irradiation zone for detection by the second detector.

Paragraph 13. The detection system of any of paragraphs 1 to 12, wherein the particle is selected from the group consisting of a droplet, a solid-phase particle, and a biological cell.

Paragraph 14. The detection system of paragraph 13, wherein the particle is a droplet disposed in an immiscible carrier liquid.

Paragraph 15. The detection system of any of paragraphs 1 to 14, wherein the detector is configured to detect light near an image plane of the mask.

Paragraph 16. The detection system of any of paragraphs 1 to 15, wherein the light deflected from the beam into the shadow region by the particle does not interact with an optical element (e.g., does not pass through a lens) between the channel and the detector.

Paragraph 17. The detection system of any of paragraphs 1 to 16, further comprising at least one source of positive/negative pressure operatively connected to the channel and configured to create a pressure differential that drives fluid flow through the channel.

Paragraph 18. The detection system of any of paragraphs 1 to 17, further comprising a source of carrier fluid disposed in fluid communication with the channel.

Paragraph 19. The detection system of paragraph 18, wherein the source of carrier fluid contains particles of interest, further comprising a source of dilution fluid in fluid communication with the channel and configured to increase a distance between particles in the channel at a position fluidically upstream of the irradiation zone by dilution of the carrier fluid containing particles of interest with the dilution fluid.

Paragraph 20. The detection system of paragraph 18 or paragraph 19, further comprising at least one source of positive/negative pressure operatively connected to the source of carrier fluid and configured to create a pressure differential that drives flow of the carrier fluid through the channel.

Paragraph 21. A detection system for particles, comprising: (A) a channel; (B) a light source configured to generate light; (C) an optical slit operatively disposed in an optical path between the light source and the channel; (D) at least one collimating element operatively disposed in an optical path between the optical slit and the channel and configured to collimate the light to form a collimated beam; (E) a line mask operatively disposed in an optical path between the collimating element and the channel, the line mask having an elongated masking region oriented parallel to the optical slit and being configured to produce a shadow region; (F) one or more focusing elements operatively disposed in an optical path between the line mask and the channel and configured to focus the collimated beam on an irradiation zone within the channel; and (G) a detector configured to detect light deflected from the beam into the shadow region by a particle passing through the irradiation zone.

Paragraph 22. A method of detecting a particle, the method comprising: (A) generating a beam of light; (B) blocking a portion of the beam optically upstream of a channel to produce a shadow region; (C) focusing the beam on an irradiation zone within the channel; (D) passing a particle through the irradiation zone, wherein the step of passing deflects light into the shadow region by interaction with the particle; and (E) detecting light in the shadow region; wherein, optionally, the step of passing temporarily causes more light to be detected.

Paragraph 23. The method of paragraph 22, wherein the step of focusing is performed on a partially blocked region of the beam that results from the step of blocking.

Paragraph 24. The method of paragraph 22 or paragraph 23, wherein the step of blocking is performed on a collimated region of the beam.

Paragraph 25. The method of any of paragraphs 22 to 24, wherein the step of blocking is performed with a mask, further comprising a step of passing light of the beam through an optical slit operatively disposed at a position optically upstream of the mask.

Paragraph 26. The method of any of paragraphs 22 to 25, wherein the step of generating light includes a step of generating light with a light-emitting diode.

Paragraph 27. The method of any of paragraphs 22 to 26, wherein the step of blocking includes a step of blocking a portion of the beam with a line mask.

Paragraph 28. The method of paragraph 27, wherein the line mask has a masking region elongated orthogonal to the channel.

Paragraph 29. The method of paragraph 28, wherein the masking region is elongated parallel to an optical slit operatively disposed upstream of the line mask.

Paragraph 30. The method of any of paragraphs 22 to 29, wherein the step of detecting is performed with a detector, further comprising a step of spatially filtering light of the beam with an optical slit disposed in an optical path between the channel and the detector.

Paragraph 31. The method of any of paragraphs 22 to 30, further comprising a step of detecting photoluminescence induced by the beam at the irradiation zone.

Paragraph 32. The method of any of paragraphs 22 to 31, wherein the step of passing a particle includes a step of passing a droplet through the irradiation zone.

Paragraph 33. The method of any of paragraphs 22 to 32, wherein the step of blocking is performed with a mask, and wherein the step of detecting is performed behind an image plane of the mask.

Paragraph 34. The method of any of paragraphs 22 to 33, wherein the step of detecting is performed with a detector, and wherein the light detected in the shadow region is not focused between the channel and the detector.

The term "about," as used herein to describe a stated value, means within 10% of the stated value. For example, a dimension described as being "about 10" means that the dimension is greater than 9 and less than 11.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

I claim:

1. A detection system for particles, comprising:
a channel;
a light source configured to generate light;
one or more optical elements configured to focus a beam of the light on an irradiation zone within the channel;
a mask operatively disposed in an optical path between the light source and the channel, wherein the mask is configured to block a portion of the beam, thereby producing a shadow region;
an optical slit operatively disposed in the optical path between the light source and the channel at a position optically upstream of the mask; and
a detector configured to detect light deflected from the beam into the shadow region by interaction with a particle passing through the irradiation zone;
wherein the mask is a line mask including a masking region elongated parallel to the optical slit and elongated orthogonal to a flow direction in the channel through the irradiation zone.

2. The detection system of claim 1, wherein the mask intersects a collimated region of the beam.

3. The detection system of claim 1, wherein the optical slit is a first optical slit, further comprising a second optical slit operatively disposed in an optical path between the irradiation zone and the detector.

4. The detection system of claim 1, wherein the detector is a first detector, further comprising a second detector configured to detect photoluminescence induced by the beam in the irradiation zone, the one or more optical elements providing an objective that collects emitted light from the irradiation zone for propagation to the second detector.

5. The detection system of claim 4, wherein the same light source generates (i) light deflected by the particle at the irradiation zone and detected by the first detector, and (ii) excitation light that induces photoluminescence in the irradiation zone for detection by the second detector.

6. The detection system of claim 1, wherein the particle is selected from the group consisting of a droplet, a solid-phase particle, and a biological cell.

7. The detection system of claim 1, wherein the detector is configured to detect light near an image plane of the mask.

8. The detection system of claim 1, further comprising a source of carrier fluid containing particles of interest and disposed in fluid communication with the channel.

9. The detection system of claim 8, further comprising a source of dilution fluid in fluid communication with the channel and configured to increase a distance between particles in the channel at a position fluidically upstream of the irradiation zone by dilution of the carrier fluid containing particles of interest with the dilution fluid.

10. The detection system of claim 1, further comprising at least one source of positive/negative pressure operatively connected to the channel and configured to create a pressure differential that drives fluid flow through the channel.

11. A method of detecting a particle, the method comprising:
generating a beam of light;
blocking a portion of the beam optically upstream of a channel to produce a shadow region;
focusing the beam on an irradiation zone within the channel;
passing a particle through the irradiation zone, wherein the step of passing deflects light into the shadow region by interaction with the particle; and
detecting light in the shadow region;
wherein the step of blocking includes a step of blocking a portion of the beam with a line mask having a masking region elongated orthogonal to the channel and elongated parallel to an optical slit operatively disposed optically upstream of the line mask.

12. The method of claim 11, wherein the step of blocking is performed on a collimated region of the beam.

13. The method of claim 11, wherein the step of detecting is performed with a detector, further comprising a step of spatially filtering light of the beam with an optical slit disposed in an optical path between the channel and the detector.

14. The method of claim 11, further comprising a step of detecting photoluminescence induced by the beam at the irradiation zone.

15. The method of claim 11, wherein the step of passing a particle includes a step of passing a droplet through the irradiation zone.

16. The method of claim 11, wherein the step of detecting is performed behind an image plane of the mask.

17. The method of claim 11, wherein the step of detecting is performed with a detector, and wherein the light detected in the shadow region is not focused between the channel and the detector.

* * * * *